United States Patent
Lawyer et al.

(10) Patent No.: US 6,262,243 B1
(45) Date of Patent: Jul. 17, 2001

(54) NUCLEIC ACIDS ENCODING ANTIMICROBIAL PEPTIDES

(75) Inventors: Carl H. Lawyer, Mequon, WI (US); Kounosuke Watabe, Springfield, IL (US)

(73) Assignee: Board of Trustees of Sothern Illinois University, Springfield, IL (US)

(*) Notice: Subject to any disclaimer, the term of this patent is extended or adjusted under 35 U.S.C. 154(b) by 0 days.

(21) Appl. No.: 09/333,441

(22) Filed: Jun. 15, 1999

Related U.S. Application Data

(62) Division of application No. 08/806,378, filed on Feb. 27, 1997, now Pat. No. 5,994,308.
(60) Provisional application No. 60/012,392, filed on Feb. 28, 1996.

(51) Int. Cl.⁷ .................................................. C07H 21/02
(52) U.S. Cl. ...................... 536/23.1; 536/23.1; 536/23.5; 530/350; 530/300; 530/324; 530/329; 514/12; 435/6; 435/7.1; 435/320.1; 435/68.1; 435/69.1
(58) Field of Search .................................... 530/350, 300, 530/324, 329; 514/12; 435/6, 7.1, 320.1, 68.1, 69.1; 536/23.1, 23.5

(56) References Cited

U.S. PATENT DOCUMENTS

| | | | |
|---|---|---|---|
| 4,399,216 | 8/1983 | Axel et al. | 435/6 |
| 4,543,252 | 9/1985 | Lehrer et al. | 514/12 |
| 4,677,063 | 6/1987 | Mark et al. | 435/68 |
| 5,202,420 | 4/1993 | Zasloff et al. | 530/324 |
| 5,210,027 | 5/1993 | Wilde et al. | 435/69.1 |
| 5,221,732 | 6/1993 | Chen et al. | 530/326 |
| 5,304,633 | 4/1994 | Tomita et al. | 530/326 |
| 5,324,716 | 6/1994 | Selsted et al. | 514/14 |
| 5,424,396 | 6/1995 | Tomita et al. | 530/329 |
| 5,432,270 | 7/1995 | Zasloff et al. | 536/23.5 |
| 5,460,954 | * 10/1995 | Lee et al. | 435/69.5 |

FOREIGN PATENT DOCUMENTS

| | | |
|---|---|---|
| 92/04462 | 3/1992 | (WO). |
| WO93/24630 | * 12/1993 | (WO). |
| WO/94/27643 | * 12/1994 | (WO). |

OTHER PUBLICATIONS

Bepler, G., et al., "Substance P Analogues Function as Bombesin Receptor Antagonists and Inhibit Small Cell Lung Cancer Clonal Growth", Peptides 9(6) 1367–1372, 1988.

Couture, R., et al., "Spinal Actions of Substance P Analogues on Cardiovascular Responses in the Rat: a Structure–Activity Analysis" Can. J. physiol. Parmacol. 65: 412–418.

Dutta, Anand S., et al., "Analogues of Substance P. Peptides Containing D–Amino Acid Residues in Various Positions of Substance P and Displaying Agonist or Receptor Selective Antagonist Effects" J. Med. Chem, 1986, 29, 1163–1171.

Dutta, Anand S., et al., "Antagonists of Substance P. Further Modifications of Substance P Antagonists Obtained by Replacing Either Positions 7, 9 or 7, 8 and 11 with D–Amino Acid Residues" J. Med. Chem 1986, 29, 1171–1178.

Lawyer et al., "Antimicrobial Activity of a13 Amino Acid Tryptophan—Rich Peptide Derived from a Putative Porcine Percursor Protein of a Novel Family of Antibacterial Peptide" FEBS Letters, vol. 390, No. 1, pp. 95–98.

Pungercar et al., "Molecular Cloning of a Putative Homolog of Proline/Arginine–Rich Antibacterial Peptides from Porcine Bone Marrow" FEBS Letters, vol. 336, No. 2, pp. 284–8, 1993.

* cited by examiner

*Primary Examiner*—Karen Cochrane Carlson
*Assistant Examiner*—Hope A. Robinson
(74) *Attorney, Agent, or Firm*—Senniger, Powers, Leavitt & Roedel

(57) ABSTRACT

A peptide which comprises a tryptophan triplet, is between 10 and 34 amino acid residues in length and exhibits antimicrobial activity is provided, together with pharmaceutical and non-pharmaceutical compositions containing, and methods utilizing, such peptides.

16 Claims, 1 Drawing Sheet

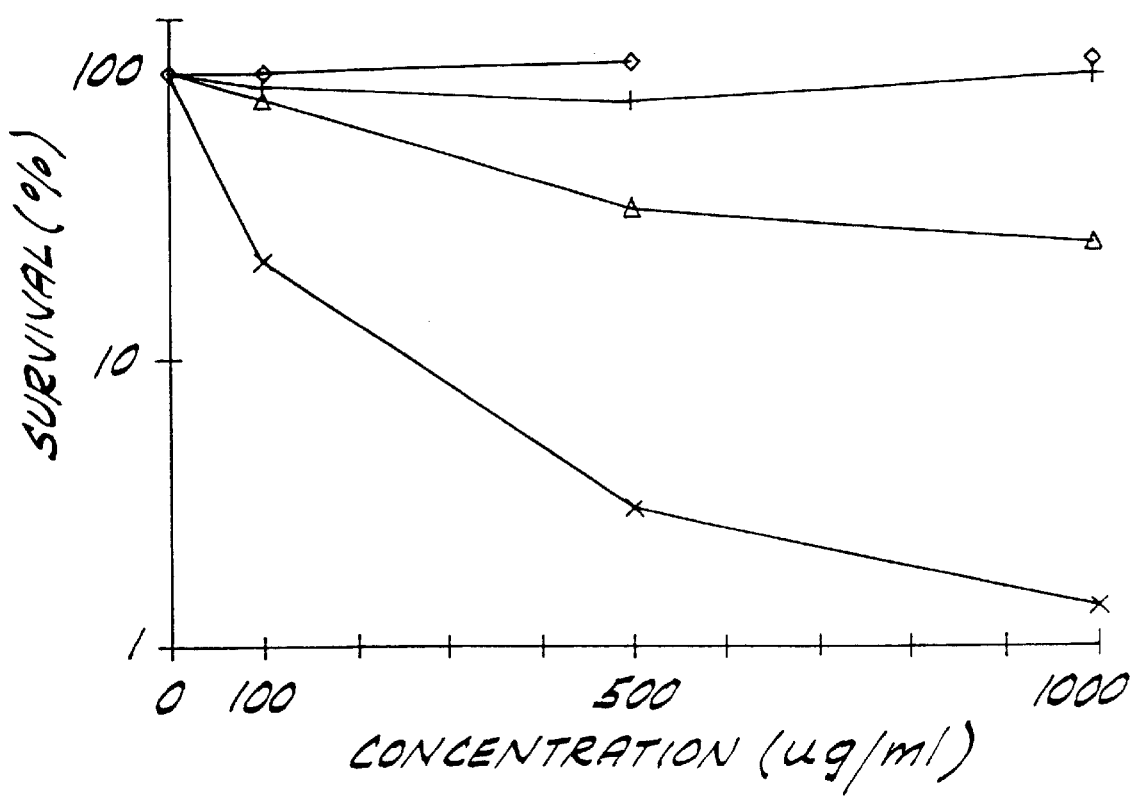

NUCLEIC ACIDS ENCODING ANTIMICROBIAL PEPTIDES

REFERENCE TO RELATED APPLICATIONS

This is a divisional of patent application Ser. No. 08/806,378, filed Feb. 27, 1997, now U.S. Pat. No. 5,994,308, which claims priority to U.S. provisional patent application Ser. No. 60/012,392, filed Feb. 28, 1996.

BACKGROUND OF THE INVENTION

This invention relates generally to antimicrobial compounds and agents. More specifically, it concerns novel broad spectrum antimicrobial peptides containing a tryptophan triplet and their derivatives which exhibit antimicrobial activity with low immunogenicity. Also provided are methods of microbicidal or microbistatic inhibition of microbial growth using pharmaceutical and non-pharmaceutical compositions wherein such antimicrobial peptides are an active component.

Infectious diseases have plagued human populations throughout history and continue to cause millions of deaths each year. Although widespread use of vaccines and drug therapy has dramatically reduced mortality due to infectious disease in developed countries, infectious diseases continue to be the leading cause of death in third world countries. It is estimated that over 600 million people are infected with tropical diseases, resulting in some 20 million deaths each year. Even in developed countries, infectious disease organisms spread misery to untold millions each year.

Individuals with an immunodeficiency disease are particularly at risk for infectious disease. The basic clinical manifestations are frequent, prolonged, severe infections, which are often caused by organisms of normally low pathogenicity. The hallmarks of immunodeficiency disease are recurrent bacterial or fungal infections. The clinical manifestations range from mild skin infections to life-threatening systematic infections. Common infectious organisms include *Staphylococcus aureas, Streptococcus pneumoniae, Escherichia coli*, and various species of Pseudomonas, Candida, and Aspergillus. Because of the seriousness of many infectious diseases, scientists continue to search for effective means of killing or controlling such organisms which, at the same time, exhibit low immunogenicity.

It has been speculated that cathelin, a protein isolated from pig blood leukocytes, is the N-terminal fragment of a pig homolog of a novel family of antibacterial peptides. The cDNA sequence of a putative homolog of this proline/arginine-rich antibacterial porcine protein was described by Joze Pungercar, et al., "Molecular cloning of a putative homolog of proline/arginine-rich antibacterial peptides from porcine bone marrow," *FEBS*, 336:284–88 (1993). However, the potentially antimicrobial portion of this proposed 228-amino acid peptide is 101 amino acids long which is too long and too large for production and effective utilization as an antimicrobial agent.

SUMMARY OF THE INVENTION

Among the several objects of the invention, therefore, may be noted the provision of broad spectrum antimicrobial peptides having low immunogenicity which can be readily synthesized; the provision of antimicrobial pharmaceutical and non-pharmaceutical compositions containing these peptides and methods of inhibiting microbial growth and treating infectious diseases using these compositions.

Briefly, therefore, the present invention is directed to broad spectrum antimicrobial peptides containing a tryptophan triplet of at least 10 amino acid residues in length. Preferably, the antimicrobial peptides of the invention have substantially the same sequence as defined by SEQ ID NO: 1. The present invention is further directed to compositions which have an antimicrobial peptide of the invention as their active component. In yet another aspect of the invention, a method of microbicidal or microbistatic inhibition of microbial growth in a microbial growth sustaining environment is provided.

Other objects and features will be in part apparent and in part pointed out hereinafter.

BRIEF DESCRIPTION OF THE DRAWINGS

FIG. 1 shows the bactericidal activities of four synthesized peptides containing tryptophan triplets. *E. coli* cells that were grown to a logarithmic phase were mixed with various concentrations of peptides, 1 (×), 2 (◀), 3 (♦) and 4 (+), in phosphate buffer. After incubation at 37° C. for 10 minutes, aliquot samples were drawn, diluted and plated on L-agar which was incubated for 18 hours. The number of colonies were then counted.

DETAILED DESCRIPTION OF THE PREFERRED EMBODIMENT

In accordance with the present invention, applicants have discovered a broad-spectrum, yet low immunogenic, antimicrobial family of peptides, distinguished in that they contain a tryptophan triplet as a part of their active site. These peptides (termed "Tritrypticin" herein) are similar to the previously unappreciated active portion of a 101 amino acid proline/arginine-rich antibacterial peptide fragment isolated from pig blood leukocytes, known as cathelin. Tritrypticin is a relatively small peptide which can be easily synthesized, yet possesses potent antimicrobial activity.

As used herein, the term "tritrypticin" refers to a tryptophan-rich peptide containing a tryptophan triplet exemplified by those peptides which have substantially the same sequence as SEQ ID NO: 1 and which exhibit antimicrobial activity.

As used herein, the term "tryptophan-rich" refers to the over-representation of tryptophan amino acids in an antimicrobial compound. The frequency of individual amino acids within a protein varies between each amino acid with tryptophan typically being the most infrequent. The average frequency of tryptophan within a randomly selected protein is about one percent. The abundance of tryptophan within a tryptophan-rich antimicrobial peptide is generally greater than twenty percent. A specific example of a tryptophan-rich peptide is the tritrypticin peptide shown as SEQ ID NO: 1 which has a tryptophan content of approximately twenty-three percent.

As used herein, the term "tryptophan triplet" refers to an amino acid sequence of three consecutive tryptophan residues. The tryptophan triplet is believed to be the rarest triplet sequence among naturally-occurring peptides.

As used herein, the term "substantially the same sequence" refers to a peptide sequence either identical to, or having functional homology with, the peptide sequence defined by SEQ ID NO: 1. It is understood that limited modifications can be made to the peptide which result in enhanced function. Likewise, it is understood that limited modifications can be made without destroying the biological function of the peptide. Such minor modification of these sequences which do not destroy the peptides antimicrobial activity also fall within this definition. Modifications can include, but are not limited to, additions, deletions or substitutions of amino acid residues, substitutions with compounds that mimic amino acid structure or function as well as the addition of chemical moieties such as amino and acetyl groups. The modifications can either be deliberate or can be accidental such as through mutation in hosts which produce tritrypticin. All of these modifications are included as long as the peptide retains its antimicrobial activity.

As used herein, the term "antimicrobial activity" refers to the ability of a compound to inhibit or irreversibly prevent the growth of a microorganism. Such inhibition or prevention can be through a microbicidal action or microbistatic inhibition. Therefore, the term "microbicidal inhibition," as used herein, refers to the ability of a compound to kill, or irreversibly damage the target organism. The term "microbistatic inhibition," as used herein, refers to the ability of the antimicrobial compound to inhibit the growth of the target microorganism without death. Microbicidal or microbistatic inhibition of microorganisms in an environment presently exhibiting microbial growth (therapeutic treatment) or an environment at risk of supporting microbial growth (prevention) is included within this definition.

As used herein, the term "microbial growth sustaining environment" refers to any fluid, substance or organism where microbial growth exists or can occur. Such environments can be, for example, humans, animals, bodily fluids, animal tissue, water, other liquids, food, food products, crops and various inanimate objects. The environment need only permit the subsistence of microbes. It does not need to promote microbial growth.

The invention is directed to broad spectrum antimicrobial peptides containing a tryptophan triplet, compositions wherein such peptides are an active component, and methods of their use to inhibit or prevent microbial growth. The peptides are at least 10 amino acid residues in length, more preferably, between 10 and 34 amino acid sequences in length, most preferably, 13 amino acid residues in length. The antimicrobial peptides of this inventions are distinguished from many antimicrobial peptides by their tryptophan-rich amino acid sequence. Further, in contrast to other tryptophan-rich peptides known in the art, such as indolicidin, tritrypticin has a novel amino acid sequence containing a tryptophan triplet. In a preferred embodiment of the invention, the antimicrobial peptide is a novel peptide with substantially the same sequence as defined by SEQ ID NO: 1.

Tritrypticin exhibits broad spectrum antimicrobial activity. Test data shows its effectiveness against such diverse classes of organisms as gram negative bacteria, gram positive bacteria, viruses and fungi. Moreover, tritrypticin is effective against microorganisms as diverse as *Escherichia coli, Pseudomonas aeruginosa, Klebsiella pneumonieae, Staphylococcus epidermidis, Proteus mirabilis*, and Streptococcus group D. Based on these initial experimental results, it is believed that tritrypticin will be similarly effective against other organisms not yet tested against.

An additional feature of tritrypticin is its low immunogenicity. Because tritrypticin is a relatively small naturally occurring peptide, there is a decreased risk of causing a host immune response over other known antimicrobial peptides.

Tritrypticin can be synthesized using conventional synthesis procedures commonly used by one skilled in the art. For example, the antimicrobial peptide of the present invention can be chemically synthesized using an automated peptide synthesizer (such as one manufactured by Pharmacia LKB Biotechnology Co., LKB Biolynk 4170 or Milligen, Model 9050 (Milligen, Millford, Mass.)) following the method of Sheppard, et al., Journal of Chemical Society Perkin I, p. 538 (1981). In this procedure, N,N'-dicyclohexylcarbodiimide is added to amino acids whose amine functional groups are protected by 9-flourenylmethoxycarbonyl (Fmoc) groups and anhydrides of the desired amino acids are produced. These Fmoc-amino acid anhydrides can then be used for peptide synthesis. A Fmoc-amino acid anhydride corresponding to the C-terminal amino acid residue is fixed to Ultrosyn A resin through the carboxyl group using dimethylaminopyridine as a catalyst. Next, the resin is washed with dimethylformamide containing piperidine, and the protecting group of the amino functional group of the C-terminal acid is removed. The next amino acid corresponding to the desired peptide is coupled to the C-terminal amino acid. The deprotecting process is then repeated. Successive desired amino acids are fixed in the same manner until the peptide chain of the desired sequence is formed. The protective groups other than the acetoamidomethyl are then removed and the peptide is released with solvent.

Alternatively, the peptides can be synthesized by using nucleic acid molecules which encode the peptides of this invention in an appropriate expression vector which include the encoding nucleotide sequences. Such DNA molecules may be readily prepared using an automated DNA sequencer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the polypeptide in a suitable host such as bacterium, e.g., *Escherichia coli*, yeast cell or mammalian cell.

It is known that certain modifications of the primary sequence shown as SEQ ID NO: 1 can be made without completely abolishing the peptide's antimicrobial activity. Modifications include the removal and addition of amino acids. Specific examples of such modifications of the present invention are shown as SEQ ID NO: 2 and SEQ ID NO: 3. Peptides containing other modifications can be synthesized by one skilled in the art and tested for retention or enhancement of antimicrobial activity using the teachings described herein. Thus, the potency of tritrypticin peptides can be modulated through various changes in the amino acid sequence or structure.

Another embodiment of the invention provides for antimicrobial compositions which have tritrypticin as an active component. In one aspect of this invention, tritrypticin is used as an active component in pharmaceutical compositions with a pharmaceutically acceptable carrier. A variety of carriers, such as buffers, can be included in the composition wherein the antimicrobial activity is retained. Such buffers, for example, include phosphate buffered saline, normal saline, and Krebs ringers solution. Compounds such as EDTA, and/or other chelating compounds, which are known to disrupt microbial membranes, can also be included in the composition. The many pharmaceutically acceptable carriers suitable for use in this invention are known to one skilled in the art.

In another aspect of this invention, tritrypticin may be used as an active component in various non-pharmaceutical compositions. In this aspect of the invention, tritrypticin can be used, for instance, as a food preservative or to inhibit potential microbial degradation. For example, shell fish and poultry routinely harbor microbes which cause severe human disease. These microbes can be inhibited with tritrypticin. Foods such as fruits and vegetables can be treated with tritrypticin to protect against microbial degradation. Tritrypticin can be administered topically or by transgenic expression of the recombinant peptide. Transgenic expression is known to one skilled in the art and can readily be performed given the nucleic acid encoding the peptide shown as SEQ ID NO: 1.

The invention also provides a method of microbicidal or microbistatic inhibition of microbial growth in a microbial growth sustaining environment. The method includes administering a microbicidally or microbistatically effective amount of tritrypticin to inhibit microbial growth. Tritrypticin can be used as a disinfectant agent to sterilize or maintain microbe-free environments. Essentially, any environment where microbial growth is undesirable can be treated with tritrypticin. Such environments include, for example, hospital, bathroom and food preparation surfaces and water supplies. Tritrypticin also can be used as a disinfectant agent to sterilize or maintain microbe free products. Examples of such products include baby wipes, diapers, bandages, towlettes, make-up products, hairspray, mouth wash, eye drops, and contact lens solutions. Effective amounts of tritrypticin to be administered will depend on the environment, target microbe and the severity of the infection or growth.

In still another embodiment of the invention, a method of treating infectious disease in a human or animal is provided. In this embodiment, tritrypticin is administered to a human or animal in microbicidally or microbistatically effective amount to inhibit microbial growth. Tritrypticin can be administered to the host subject by, for example, intravenous injection, intraperitoneal injection, orally, topically, or by way of nebulizer or aerosol spray composition. Lipid vesicles or emulsion preparations containing tritrypticin can also be used for administering tritrypticin to humans or animals. Specific modes of administration will depend on the microorganism to be targeted. The best mode of administration for the particular application will be readily apparent to one skilled in the art.

One skilled in the art will know the effective amount of tritrypticin to be administered for a desired method given the teachings described herein.

The following examples illustrate the invention.

EXAMPLE I

Radial diffusion assay were performed using double-layered agarose as described by Lehrer et al., "Ultrasensitive assays for endogenous antimicrobial polypeptides," J. Immunol. Methods 137, 167–73 (1991), with minor modifications. Briefly, $2\times10^5$ cells of mid-log phase bacteria grown in TSB medium were mixed with 1.0% agarose in 10 mM sodium phosphate buffer (pH 7.4) containing 0.02% Tween 20 and 0.03% TSB. The mixture was then poured into a petri dish. When the agarose was solidified, wells with 2.5 mm in diameter were made in the agarose and samples of the peptides in various concentrations were placed in each of the wells. The plate was incubated at 37° C. for 2 hours. Top agar containing 1.0% agarose in 10 mM sodium phosphate buffer (pH 7.4) and 6% TSB was poured over it and the plate was further incubated at 37° C. for 18 hours. The diameters of the inhibitory zones were measured for the quantitation of inhibitory activities.

As shown in Table I, Peptide 1, with the sequence of SEQ ID NO: 1, showed strong antibacterial effects on *Escherichia coli* when tested by the radial diffusion assay. Several derivatives of this peptide, named Peptide 2, 3, and 4, also shown in Table I were then synthesized and tested by radial diffusion, as described above, against *E. coli*. Peptide 2 contained arginine at both ends and showed slightly higher activity than Peptide 1. Peptide 3, which shared 9 amino acids with peptide 1, showed detectable but significantly less activity than that of Peptide 1. Peptide 4 which shared 7 amino acid residues with Peptide 1 had no detectable activity.

TABLE 1

ZONE INHIBITION ASSAY WITH *E. COLI*

| Peptide | Amino Acid Sequence | Inhibitory Activity at 50 μg/well | Inhibitory Activity at 5 μg/well |
| --- | --- | --- | --- |
| Peptide 1 | VRRFPWWWPFLRR | 10 | 6 |
| Peptide 2 | RRRFPWWWPFLRRR | 11 | 7 |
| Peptide 3 | RFPWWWPFLR | 5 | 2 |
| Peptide 4 | FPWWWPF | 0 | 0 |

EXAMPLE II

The antimicrobial effects of the above peptides on other gram positive and negative bacteria including Pseudomonas, Klebsiella, Staphylococcus, Proteus and Streptococcus were then tested using the method described in example 1. As shown in Table II, Peptide 1 showed a broad range of antimicrobial activity on all organisms tested except *Proteus mirabilis*. Again, Peptide 2 showed slightly higher activity on those same bacteria, while Peptide 3 showed low, but detectable, activity and Peptide 4 had no activity on any organisms.

TABLE 2

ZONE INHIBITION ASSAY WITH GRAM+ AND GRAM− BACTERIA

| Microorganism | Peptide 1 | Peptide 2 | Peptide 3 | Peptide 4 |
| --- | --- | --- | --- | --- |
| *Escherichia coli* | 5 | 5 | 2 | 0 |
| Pseudomonas | 3 | 4 | 1 | 0 |
| Klebsiella | 7 | 7 | 2 | 0 |
| Staphylococcus | 5 | 7 | 0 | 0 |
| Proteus | 1 | 2 | 0 | 0 |
| Streptococcus | 4 | 5 | 1 | 0 |

EXAMPLE III

In order to examine whether the antimicrobial activities of the peptides are bacteriostatic or bactericidal, bactericidal assay for all peptide using *Escherichia coli* were performed. Cells were incubated with various concentration of peptides in sodium phosphate buffer. After incubation for 10 minutes, aliquot samples ($2\times10^5$) were drawn and mixed with various concentrations of the peptides in 20 μl of sodium phosphate buffer. The mixtures were incubated at 37° C. and samples were withdrawn at 10 minute intervals, diluted with sodium phosphate buffer and plated on L-agar plates. After overnight incubation of the plates at 37° C., the number of colonies were counted. The results are shown in FIG. 1. The number of survived cells were then counted. As shown in FIG. 1, Peptide 1 showed strong bactericidal activity and 97% of cells were killed within 10 minutes at a concentra tion of 50 μg/ml. Peptide 2 showed significantly less bactericidal activity and Peptides 3 and 4 showed minimum activity. These results suggest that the antimicrobial activity of the peptides shown by radial diffusion assay is bactericidal. However, it should be noted that the antimicrobial activity of Peptide 2 by radial diffusion assay was stronger than that of Peptide 1, while the bactericidal activity of Peptide 2 is significantly less than that of Peptide 1. Therefore, the mechanism of antimicrobial activity of Peptide 1 and 2 appears to differ due to the modification of the arginine residues present at both ends of Peptide 2.

EXAMPLE IV

Because Peptide 1 showed broad spectrum antimicrobial activity, the effect of the peptides on two fungi, namely *Aspergillus fumigates* and *Candida albicans* was tested. As shown in Table III, Peptide 1 inhibited the growth of Aspergillus and Candida completely at a concentration of 250 μg/ml and 1000 μg/ml, respectively. Peptide 2 also inhibits the growth of both fungal strains at a similar concentration. Peptide 3 and 4 also showed growth inhibitory effects on *Aspergillus fumigatus* at a concentration of 500 μg/ml, but they had no inhibitory effect on *Candida albicans*. These results suggest that Peptide 1 and Peptide 2 could be effective antifungal drugs though the required concentration is higher than for bacteria.

TABLE 3

FUNGICIDAL ASSAY
MINIMUM INHIBITORY CONCENTRATION

| Peptides | Aspergillus fumigatus | Candida albicans |
| --- | --- | --- |
| Peptide 1 | 250 μg/ml | 1000 μg/ml |
| Peptide 2 | 250 μg/ml | 1000 μg/ml |
| Peptide 3 | 500 μg/ml | >1000 μg/ml |
| Peptide 4 | 500 μg/ml | >1000 μg/ml |

EXAMPLE V

The minimum inhibitory concentration (MIC) was determined by growing fungal strains in YG media until the fungi reached logarithmic phase. The cells were diluted in YG medium then placed in a 96-well plate along with a series of 2-fold dilutions of the peptides. The plate was then incubated at 37° C. for 24 hours. Minimum inhibitory growth was defined as the lowest concentration at which there was no fungal growth.

In view of the above, it will be seen that the several objects of the invention are achieved.

As various changes could be made in the above compositions and methods without departing from the scope of the invention, it is intended that all matter contained in the above description shall be interpreted as illustrative and not in a limiting sense.

What is claimed is:

1. An isolated nucleic acid molecule which encodes an antimicrobial peptide which peptide contains a tryptophan triplet, is between 10 and 34 amino acid residues in length, and exhibits antimicrobial activity.

2. The isolated nucleic acid molecule of claim 1, wherein the peptide is selected from the group consisting of SEQ ID NO: 1, SEQ ID NO: 2, and SEQ ID NO: 3.

3. A recombinant vector, comprising the nucleic acid molecule of claim 1.

4. A recombinant vector, comprising the nucleic aid molecule of claim 2.

5. The recombinant vector of claim 3, wherein the vector is an expression vector.

6. The recombinant vector of claim 4, wherein the vector is an expression vector.

7. A host cell transformed with the recombinant vector of claim 3.

8. A host cell transformed with the recombinant vector of claim 4.

9. A host cell transformed with the recombinant vector of claim 5.

10. A host cell transformed with the recombinant vector of claim 6.

11. The host cell of claim 3, wherein the host cell is *Esherichia coli*, a yeast cell, or a mammalian cell.

12. The host cell of claim 8, wherein the host cell is *Esherichia coli*, a yeast cell, or a mammalian cell.

13. The host cell of claim 9, wherein the host cell is *Esherichia coli*, a yeast cell, or a mammalian cell.

14. The host cell of claim 10 wherein the host cell is *Esherichia coli*, a yeast cell, or a mammalian cell.

15. A method of producing a peptide wherein the peptide contains a tryptophan triplet, is between 10 and 34 amino acid residues in length, and exhibits antimicrobial activity, the method comprising:
   (a) obtaining the host cell of claim 9; and
   (b) growing the host cell under conditions and for a time sufficient to produce the peptide.

16. A method of producing a peptide wherein the peptide contains a tryptophan triplet, is between 10 and 34 amino acid residues in length, and exhibits antimicrobial activity, the method comprising:
   (a) obtaining the host cell of claim 10; and
   (b) growing the host cell under conditions and for a time sufficient to produce the peptide.

* * * * *

SEQUENCE LISTING

```
<160> NUMBER OF SEQ ID NOS:  4

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthesized
      Proteins

<400> SEQUENCE: 1

Val Arg Arg Phe Pro Trp Trp Trp Pro Phe Leu Arg Arg
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthesized
      Proteins

<400> SEQUENCE: 2

Arg Arg Arg Phe Pro Trp Trp Trp Pro Phe Leu Arg Arg Arg
 1               5                  10

<210> SEQ ID NO 3
<211> LENGTH: 10
<212> TYPE: PRT
```

```
<213> ORGANISM: Artificial Sequence
<220> FEATURE:
<223> OTHER INFORMATION: Description of Artificial Sequence: Synthesized
      Proteins

<400> SEQUENCE: 3

Arg Phe Pro Trp Trp Trp Pro Phe Leu Arg
 1               5                   10

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthesized
      Sequence

<400> SEQUENCE: 4
tcaggagatt tccctggtgg tggccgttcc tacgaagac                            39
```